US007541355B2

(12) United States Patent
Wei et al.

(10) Patent No.: US 7,541,355 B2
(45) Date of Patent: Jun. 2, 2009

(54) CONVERSION PROCESS FOR 2,3-BENZODIAZEPINE ENANTIOMERS

(75) Inventors: Yong Victoria Wei, Branchburg, NJ (US); Naidaong Ye, Malvern, PA (US); Kimm Galbraith, Spring City, MD (US); Jianfeng Shi, Baltimore, MD (US); Wuyi Wang, Silver Spring, MD (US); Yungen Xu, Baltimore, MD (US); Mallikarjun Reddy Ravi, Baltimore, MD (US)

(73) Assignee: Vela Acquisition Corporation, Iselin, NJ (US)

( * ) Notice: Subject to any disclaimer, the term of this patent is extended or adjusted under 35 U.S.C. 154(b) by 552 days.

(21) Appl. No.: 11/135,100

(22) Filed: May 23, 2005

(65) Prior Publication Data
US 2006/0264421 A1    Nov. 23, 2006

(51) Int. Cl.
*A61P 25/22* (2006.01)
*A61K 31/551* (2006.01)
*C07D 243/02* (2006.01)

(52) U.S. Cl. ................... 514/221; 540/567
(58) Field of Classification Search .............. 514/221; 540/567
See application file for complete search history.

(56) References Cited

U.S. PATENT DOCUMENTS

| 3,736,315 | A | 5/1973 | Korosi et al. ............... 260/239 |
| RE30,014 | E | 5/1979 | Körosi et al. ............... 260/239 |
| 4,322,346 | A | 3/1982 | Kórósi et al. ............... 260/239 |
| 4,423,044 | A | 12/1983 | Körösi et al. ............... 424/244 |
| 5,426,215 | A | 6/1995 | Bertrand et al. ............. 562/401 |
| 5,621,117 | A | 4/1997 | Bethge et al. ................ 549/39 |
| 6,080,736 | A | 6/2000 | Landry et al. ............... 514/221 |
| 6,080,887 | A | 6/2000 | Drauz et al. ................. 562/401 |
| 6,133,446 | A | 10/2000 | TenBrink et al. ............ 546/196 |
| 6,458,955 | B1 | 10/2002 | Gattuso ....................... 546/201 |
| 6,638,928 | B1 | 10/2003 | Harris et al. ................. 514/221 |
| 6,649,607 | B2 | 11/2003 | Leventer et al. ............. 514/221 |
| 6,683,072 | B1 | 1/2004 | Kucharik et al. ....... 514/211.13 |
| 6,864,251 | B2 | 3/2005 | Kucharik et al. ............ 514/221 |
| 7,022,700 | B2 | 4/2006 | Harris et al. ................. 514/221 |
| 2004/0106602 | A1 | 6/2004 | Kucharik et al. ............ 514/221 |
| 2004/0138209 | A1 | 7/2004 | Kucharik et al. ............ 514/221 |
| 2004/0138210 | A1 | 7/2004 | Harris et al. ................. 514/221 |
| 2004/0152695 | A1 | 8/2004 | Harris et al. ................. 514/221 |
| 2004/0157833 | A1 | 8/2004 | Harris et al. ................. 514/221 |
| 2004/0162284 | A1 | 8/2004 | Harris et al. ................. 514/221 |
| 2004/0224943 | A1 | 11/2004 | Leventer et al. ............. 514/221 |
| 2004/0229867 | A1 | 11/2004 | Kucharik ..................... 514/221 |
| 2004/0254174 | A1 | 12/2004 | Perrin et al. ................. 514/221 |
| 2005/0075329 | A1 | 4/2005 | Leventer et al. ............. 514/221 |
| 2005/0288277 | A1 | 12/2005 | Kucharik et al. ............ 514/221 |

FOREIGN PATENT DOCUMENTS

| HU | 178516 | 3/1983 |
| HU | 178519 | 3/1983 |
| WO | WO 00/24400 | 5/2000 |

OTHER PUBLICATIONS

I. Fitos, et al., "Separation of Enantiomers of Benzodiazepines on the Chiral-AGP Column" *Journal of Chromatography A*, 1995, 709, 265-73.
E. Fogassy, et al., "Studies on the Proerties and Structure of Optically Active 1-(3,4-Dimethoxyphenyl)-4-methyl-5-ethyl-7,8-dimethoxy-5H-2,3-Benzodiazepine (Tofisopam)." in H.C. Van der Plas, et al. (Eds.) "Bio-Organic Heterocycles Synthetic, Physical Organic and Pharmacological Aspects", Elsevier, Amsterdam (1984).
E. J. Horvath, et al., "Anxiolytic 2,3-benzodiazepines, their specific binding to the basal ganglia", *Progress in Neurobiology*, 2000, 60, 309-42.
M. Rizzo, "Chromatographic separation of 2,3-benzodiazepines" *Journal of Chromatography B*, 2000, 747, 203-16.
M. Simonyi, et al. "Stereoselective Binding of a 2,3-Bezodiazepine to Human Serum Albumin", *Biochemical Pharmacology*, 1993, 32(12), 1917-20.
G. Toth, et al., Racemic Resolution of (+)-5-Ethyl-1(3,4-Dimethoxyphenyl)-6,7-Dimethoxy-4-Methyl-5H-2,3-Benzodiazepine and Anomalous Chiroptic Behavior of the Enantiomers (1), *J. Heterocyclic Chem.*, 1983, 20, 709-13.
J. Visy, et al., "The Role of Configuration and Conformation in the Binding of 2,3-Benzodiazepines to Human Serum Albumin" *Chirality*, 1989, 1, 271-75.

*Primary Examiner*—Brenda L Coleman
(74) *Attorney, Agent, or Firm*—Daniel A. Monaco; Drinker Biddle & Reath LLP

(57) ABSTRACT

Methods for the racemization of an enantiomer of a 2,3-benzodiazepine molecule into the corresponding racemic mixture under either basic or acidic conditions are described. Furthermore, the invention relates to the conversion of an enantiomer of tofisopam or its metabolites to the corresponding opposite enantiomer.

18 Claims, 1 Drawing Sheet

CONVERSION PROCESS FOR 2,3-BENZODIAZEPINE ENANTIOMERS

BACKGROUND OF THE INVENTION

Tofisopam (1-(3,4-dimethoxyphenyl)-4-methyl-5-ethyl-7, 8-dimethoxy-5H-2,3-benzodiazepine) is an exemplary 2,3-benzodiazepine molecule. Tofisopam is a non-sedative anxiolytic that has no appreciable sedative, muscle relaxant or anticonvulsant properties (Horvath et al., *Progress in Neurobiology*, 60 (2000), 309-342). In addition, tofisopam has been employed in the treatment of gastrointestinal disorders, including irritable bowel syndrome, and has been used in the treatment of menopausal symptoms.

Tofisopam is a racemic mixture of (R)- and (S)-enantiomers. The chiral nature of tofisopam is due to the asymmetric carbon, at the 5-position of the benzodiazepine ring, attached with four different groups. Differential therapeutic effects have been noted for either enantiomer. For example, the (R)-enantiomer of tofisopam has been isolated and shown to possess the nonsedative anxiolytic activity of the racemic mixture. See U.S. Pat. No. 6,080,736; the entire disclosure of which is incorporated herein by reference. Furthermore, the (R)-enantiomer has been shown to have a differential effect in the treatment of leukotriene B4-mediated disease. See U.S. Pat. No. 6,864,251; the entire disclosure of which is incorporated by reference. The (S)-enantiomer has been isolated and shown to possess an anticonvulsant activity. See U.S. Pat. No. 6,649,607; the entire disclosure of which is incorporated herein by reference. Similarly, the (S)-enantiomer has been shown to be effective in lowering body temperature, as in minimizing hot flashes. See US Patent Publication 20040229866; the entire disclosure of which is incorporated herein by reference.

Therefore, it is frequently desirable to obtain one enantiomer substantially free of the other enantiomer in high yield. Present methodologies for preparing an isolated enantiomer result in the generation of a large amount of the undesired enantiomer. The present invention converts the undesired enantiomer to the desired enantiomer to increase the yield of the desired enantiomer.

SUMMARY OF THE INVENTION

The present invention encompasses methods for increasing the yield of a desired enantiomer of a 2,3-benzodiazepine molecule from a racemic mixture. In a first method, the method comprises (a) obtaining the undesired enantiomer, (b) reacting the undesired enantiomer with one or greater base equivalent of an organic base at a temperature below 20° C., (c) quenching the reaction with a proton source thereby obtaining a racemate from the undesired enantiomer, and (d) isolating the desired enantiomer from the racemate of step (c). In a second method, the method comprises (a) obtaining the undesired enantiomer, (b) reacting the undesired enantiomer with an organic or inorganic acid at an elevated temperature in an elevated temperature boiling organic solvent thereby obtaining a racemate from the undesired enantiomer, and (c) isolating the desired enantiomer from the racemate of step (b).

The present invention further encompasses methods for racemizing an undesired enantiomer. In a first method, the method comprises (a) reacting the undesired enantiomer with one or greater base equivalent of an organic base at a temperature below 20° C., and (b) quenching the reaction with a proton source thereby obtaining a racemate from the undesired enantiomer. In a second method, the method comprises reacting the undesired enantiomer with an organic or inorganic acid at an elevated temperature in a high temperature boiling organic solvent thereby obtaining a racemate from the undesired enantiomer.

DESCRIPTION OF THE INVENTION

Figure 1:
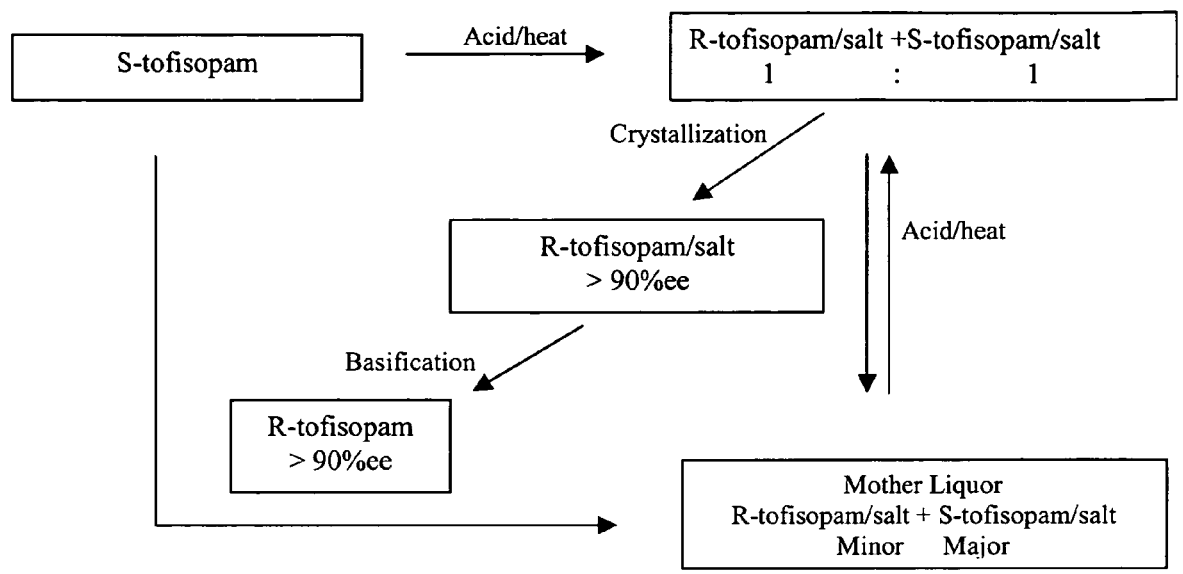
FIG. 1 illustrates an exemplary continuous method for converting an undesired enantiomer to the desired enantiomer by racemizing the undesired enantiomer and then further isolating the desired enantiomer from the resulting racemate.

The present invention provides a method for increasing the yield of a desired enantiomer of a 2,3-benzodiazepine molecule under basic or acidic conditions. In one embodiment, the desired enantiomer is (R)-tofisopam or one of its metabolites or its analogs. In another embodiment, the desired enantiomer is (S)-tofisopam or one of its metabolites or its analogs. The method comprises (a) obtaining the undesired enantiomer, (b) reacting the undesired enantiomer with one or greater base equivalent of an organic base at a temperature below 20° C., (c) quenching the reaction with a proton source thereby obtaining a racemate from the undesired enantiomer, and (d) isolating the desired enantiomer from the racemate of step (c).

The 2,3-benzodiazepines of the present invention may be prepared by one of several methods. These methods generally follow the synthetic strategies and procedures used in the synthesis of racemic 2,3-benzodiazepines, such as tofisopam and tofisopam analogs. See U.S. Pat. Nos. 3,736,315 and 4,423,044 (tofisopam syntheses) and Horvath et al., *Progress in Neurobiology* 60(2000) p. 309-342 and references cited therein (preparation of tofisopam and analogs thereof), the entire disclosures of which are incorporated herein by reference.

A number of methods are known in the art for isolating undesired enantiomer from the desired enantiomer from a racemic mixture. Racemic 2,3-benzodiazepines may, for example, be converted to the (S)-dibenzoyltartaric acid salt, which is a diastereomeric mixture of SS and RS configurations. The pair of diastereomers (R,S) and (S,S) possess different properties, e.g., differential solubilities, that allow for the use of conventional separation methods. Fractional crystallization of diastereomeric salts from a suitable solvent is one such separation method. This resolution has been successfully applied to the resolution of racemic tofisopam. See Hungarian Patent 178516 and also Toth et al., *J. Heterocyclic Chem.*, 20:09-713 (1983), the entire disclosures of which are incorporated herein by reference.

Alternatively, racemic-2,3-benzodiazepines may be derivatized via, for example, acylation of an aryl hydroxy moiety, with a chiral acylating reagent, e.g., (S)-mandelic acid. The resulting ester, has a second chiral center, and thus exists as a diastereomeric pair separable using conventional methods such as crystallization or chromatography. Following the separation, the chiral moiety with which the racemic 2,3-benzodiazepine is derivatized, may be removed.

Racemic 2,3-benzodiazepines may be separated without diastereomer formation by differential absorption on a chiral stationary phase of a chromatography column, particularly a preparative HPLC column. Chiral HPLC columns are commercially available with a variety of packing materials to suit a broad range of separation applications. Exemplary stationary phases suitable for resolving the racemic 2,3-benzodiazepines include:

(i) macrocyclic glycopeptides, such as silica-bonded vancomycin which contains 18 chiral centers surrounding three pockets or cavities;

(ii) chiral alpha,-acid glycoprotein;

(iii) human serum albumin; and (iv) cellobiohydrolase (CBH).

Chiral alpha$_1$-acid glycoprotein is a highly stable protein immobilized onto spherical silica particles that tolerates high concentrations of organic solvents, high and low pH, and high temperatures. Human serum albumin, though especially suited for the resolution of weak and strong acids, zwitterionic and nonprotolytic compounds, has been used to resolve basic compounds. CBH is a very stable enzyme which has been immobilized onto spherical silica particles and is preferentially used for the separation of enantiomers of basic drugs from many compound classes.

The resolution of tofisopam by chiral chromatography using macrocyclic glycopeptide as a stationary phase on a Chirobiotic V™ column (ASTEAC, Whippany, N.J.) is disclosed in U.S. Pat. No. 6,080,736. Fitos et al. (*J. Chromatogr.*, 709 265 (1995)), discloses another method for resolving racemic tofisopam by chiral chromatography using a chiral alpha$_1$-acid glycoprotein as a stationary phase on a CHIRAL-AGP™ column (ChromTech, Cheshire, UK). These chromatographic methods, may be used generally to separate racemic 2,3-benzodiazepines of formula I into individual (R)- and (S)-enantiomers. The Chirobiotic V™ column is available in a semi-preparative size as employed for the above separation 500 mm×10 mm). The stationary phase of the Chirobiotic V™ column is commercially available in bulk for packing of preparative chromatography columns with larger sample capacity.

In one method, once the enantiomers have been separated, the undesired enantiomer is obtained and reacted with one or greater base equivalent of a organic base at a temperature below 20° C. Previously, Toke et al (Hungarian Patent No. 178519) showed that (R)-tofisopam could be converted to (S)-tofisopam by racemizing in a polar solvent, preferably dimethylformamide, in the presence of a basic catalyst, most effectively potassium tertiary butoxide, between 20-150° C., optimally 100° C., for 5 hours. The starting material was about 89% (R)-tofisopam and the product from the racemization process was about 74% (R)-tofisopam. So the process needed to be repeated several times to obtain a racemate (50% (R)-tofisopam: 50% (S)-tofisopam). On the other hand, the process we developed is initiated with purer enantiomer (97% (S)-tofisopam) and results within two hours in a racemate (50% (S)-tofisopam; 50% (R)-tofisopam). The developed method requires reacting the undesired enantiomer in a polar solvent, with one or greater base equivalent of organic base at a temperature below 25° C., preferably below 20° C. Then the reaction is quenched with a proton source.

In another method, the undesired enantiomer is obtained and is reacted with a organic or inorganic acid at an elevated temperature in a high temperature boiling organic solvent. By this method similarly good racemization results are obtained. Once the racemization process is complete, the racemate may be subjected to further cycles to separate the desired enantiomer and the undesired enantiomer along with further racemization of the undesired enantiomer.

Furthermore, the racemization processes outlined above may be incorporated into a continuous racemization/enantiomer separation process, such as illustrated in FIG. 1 as an example. In FIG. 1, (S)-tofisopam (the undesired enantiomer) is racemized to a 50:50 mixture of (S)-tofisopam and (R)-tofisopam under acidic conditions and heat. Then (R)-tofisopam (the desired enantiomer) is selectively isolated (such as by crystallization/basification) and the mother liquor containing excess undesired (S)-tofisopam is racemized again.

The practice of the invention is illustrated by the following non-limiting examples.

EXAMPLES

Example 1

Preparation and Isolation of (S)-Tofisopam

A. Synthesis of Racemic Tofisopam:

4.41 g (10 mmol) of 1-(3,4-dimethoxyphenyl)-3-methyl-4-ethyl-6,7-dimethoxyisobenzopyrilium chloride hydrochloride is dissolved in methanol (35 mL) at a temperature of 40° C. After cooling to 20-25° C., hydrazine hydrate (0.75 g, 15 mmol, dissolved in 5 mL methanol) is added. The reaction is monitored by HPLC and when complete, is evaporated to dryness. The residue is triturated with cold water (3 mL), filtered and dried to yield the crude (R,S)-1-(3,4-dimethoxyphenyl)-4-methyl-5-ethyl-7-hydroxy-8-methoxy-5H-2,3-benzo-diazepine which is subsequently triturated with hot ethyl acetate to yield the pure product.

B. Resolution of Racemic Tofisopam to Produce (S)-Tofisopam:

The enantiomers of tofisopam were resolved by chiral chromatography. For example, tofisopam (42.8 mg dissolved in acetonitrile (ACN)) was loaded onto a Chirobiotic V column (ASTEC, Whippany, N.J.). Elution of the compounds with methyl-tert-butyl ether (MTBE)/ACN 90/10 (v/v), 40 mL/min, was monitored at 310 nm, 2 mm path. The R(−) enantiomer was the first compound to elute from the column. R(−) tofisopam ("peak A"'), S(−/+) tofisopam ("peak B" and "peak B'"), and residual R(+) tofisopam ("A") co-eluted and were collected in a subsequent fraction.

The S(−) enantiomer was isolated from fraction 2 by the following protocol. Fraction 2 was dried, redissolved in 1 mL of ACN and loaded onto a Chirobiotic V column. Peak B and B' was shave recycled over a Chirobiotic V column two more times (MTBE/ACN 90/10 (v/v), 40 mL/min monitored at 310 nm, 2 mm path). A peak containing S(−) tofisopam was collected from the third recycle, dried and stored for use in biological assays.

Achiral and chiral HPLC analyses for the S-tofisopam starting material were performed. The results showed that the R:S ratio for the starting material was 3:97.

Example 2

Racemization Under Basic Conditions

To a solution containing S-tofisopam dissolved in anhydrous tetrahydrofuran (THF) was slowly added an organic base (1 to 2 equivalents) under nitrogen at different temperature ranges. After 2 hrs the reaction was quenched with a proton source (3 to 5 equivalents) and the solvent was evaporated. The residue was dissolved in ethyl acetate (EtOAc) and washed with water. The organic layer was separated, dried over sodium sulfate, and concentrated to furnish a yellow solid (material recovery: ~97%). The crude product was triturated in methanol for initial purification. Further purification can be achieved by chromatography. The reaction was monitored by chiral HPLC.

Eight organic bases with different degree of basicity, metal counter ion, and coordination features under various reaction conditions were investigated. These bases included n-butyl lithium (n-BuLi), sec-butyl lithium (sec-BuLi), sodium hydride (NaH), potassium hydride (KH), sodium methoxide, potassium t-butyloxide/n-butyl lithium, lithium diisopropylamide (LDA), and potassium t-butyloxide (KOtBu). Four different reaction temperature ranges were evaluated, including (1) −78° C., (2) −78° C. to 0° C., (3) −78° C. to room temperature (RT), and (4) 0° C. to RT.

Best results were obtained using non-coordinating sodium and potassium bases in the temperature range 0° C. to RT. More effective deprotonation was observed with these bases compared with lithium bases. Exemplary results are summarized in Table 1.

TABLE 1

Summary of the conversion of S-tofisopam to R-tofisopam with sodium and potassium bases

| Base/proton source | Temp (° C.) | Equivalent of Base | Reaction time | HPLC Enantiomeric ratio (S/R) |
|---|---|---|---|---|
| NaH/$D_2O$ | 0° C. to RT | 2 | 2 hrs | 97:3 |
| KH/$D_2O$ | 0° C. to RT | 2 | 2 hrs | 97:3 |
| NaOMe/$D_2O$ | 0° C. to RT | 2 | 2 hrs | 96:4 |
| KOtBu/n-BuLi/$D_2O$ | 0° C. to RT | 2 | 2 hrs | 96:4 |
| KOtBu/$D_2O$ | 0° C. to RT | 1 | 2 hrs | 97:3 |
| KOtBu/$D_2O$ | 0° C. to RT | 2 | 2 hrs | 1:1 |
| KOtBu/$H_2O$ | 0° C. to RT | 2 | 2 hrs | 1:1 |

As shown in Table 1, NaH, KR, NaOMe, or KOtBu/nBuLi did not yield significant shift to the R enantiomer. However, KOtBu produced complete racemization under otherwise similar conditions. Basicity and base solubility may both play roles in the deprotonation step. The experiment also indicated that two fold of base was necessary to achieve complete racemization. The deprotonation was highly regioselective. Racemic tofisopam was obtained as the only product and no material was lost after workup.

Example 3

Exemplary Procedure for the Conversion of S-Tofisopam to Racemic Tofisopam Under Basic Condition To a solution containing S-tofisopam (10 g, 26.1 mmol) dissolved in 100 mL of THF was slowly added KOtBu powder (5.84 g, 52.1 mmol) under nitrogen at 0° C. and the resulting solution was stirred at room temperature. After 2 hrs the reaction was quenched with water (0.94 mL, 52.1 mmol) or R-camphorsultam (52.1 mmol), and the solvent was evaporated. The residue was dissolved in ethylacetate (EtOAc) (200 mL) and washed with water. The organic layer was dried over sodium sulfate and concentrated to furnish a yellow solid, 9.7 g. The crude product was triturated in methanol for initial purification. Further purification can be achieved by chromatography.

The validity of this procedure was confirmed by three batches, at 0.1 g, 6 g and 10 g scale respectively. In all these reactions, racemic tofisopam mixture was obtained in >97% yield.

Example 4

Acid Catalyzed Racemization of (S)-Tofisopam

A racemization study was performed with several acids: camphor sulfonic acid (CSA), paratoluenesulfonic acid (pTSA), tartaric acid, dibenzoyl-D/L-tartaric acid (DDTA/DLTA), and acetic acid. Several commonly organic solvents with different polarity and boiling point ranges, such as tetrahydrofuran (THF), toluene, dimethylsulfoxide (DMSO), dioxane, ethyleneglycol dimethyl ether (glyme), dimethylformamide (DMF), alcohols, and water were used to study the solvent effect.

The general reaction condition was as follows: S-tofisopam (0.3 M) and an acid (~0.3 M) was mixed in a solvent and heated to a specified temperature for a given time (3~16 h). Samples were taken out and submitted for HPLC analysis. Table 2 provides a summary of the results.

TABLE 2

Summary of the reaction condition to convert S-tofisopam to the racemate

| Experiment | Acid (eq) | Solvent | Temp ° C. | Reaction Time | S:R ratio by HPLC |
|---|---|---|---|---|---|
| 1 | S-CSA (1eq) | THF | Reflux (67° C.) | 3 hrs | 88:12 |
| 2 | S-CSA (1eq) | THF | Reflux | 3 hrs | 89:11 |
| 3 | L-tartaric (1eq) | THF | Reflux | 3 hrs | 97:03 |
| 4 | p-TSA (1eq) S-CSA (1eq) | THF | Reflux | 3 hrs | 93:07 |
| 5 | L-tartaric (1eq)/ KOH (1eq) | THF | Reflux | 3 hrs | 97:03 |
| 6 | p-TSA (1eq) | THF | Reflux | 3 hrs | 93:07 |
| 7 | p-TSA (1eq)/ R-CSA (0.2eq) | THF | Reflux | 3 hrs | 93:07 |
| 8 | DDTA (1eq) | Dioxane | Reflux (105° C.) | 4 hrs | 52:48 |
| 9 | DDTA (1eq) | Glyme | Reflux (85° C.) | 4 hrs | 67:33 |
| 10 | Acetic acid (1eq) | Dioxane | Reflux | 3 hrs | 97:03 |
| 11 | S-CSA (1eq) | Toluene | 120° C. | 8 hrs | 55:45 |
| 12 | R-CSA (1eq) | Toluene | 120° C. | 8 hrs | 53:47 |
| 13 | S-CSA (1eq) | Dioxane | 100° C. | 8 hrs | 53:47 |
| 14 | R-CSA (1eq) | Dioxane | 100° C. | 8 hrs | 54:46 |
| 15 | L-Tartaric acid (1eq) | Toluene | 120° C. | 8 hrs | 91:9 |
| 16 | L-Tartaric acid (1eq) | Dioxane | 100° C. | 8 hrs | 80:20 |
| 17 | S-CSA (1eq) | DMF | 140° C. | 6 hrs | 72:28 |
| 18 | R-CSA (1eq) | DMF | 140° C. | 6 hrs | 68:32 |
| 19 | S-CSA (1eq) | DMSO | 140° C. | 6 hrs | 55:45 |
| 20 | R-CSA (1eq) | DMSO | 140° C. | 6 hrs | 54:46 |

TABLE 2-continued

Summary of the reaction condition to convert S-tofisopam to the racemate

| Experiment | Acid (eq)   | Solvent       | Temp ° C. | Reaction Time | S:R ratio by HPLC |
|------------|-------------|---------------|-----------|---------------|-------------------|
| 21         | S-CSA (1eq) | H₂O           | 100° C.   | 16 hrs        | 86:14             |
| 22         | R-CSA (1eq) | H₂O           | 100° C.   | 16 hrs        | 85:15             |
| 23         | S-CSA (1eq) | H₂O/Toluene   | 100° C.   | 16 hrs        | 95:05             |
| 24         | R-CSA (1eq) | H₂O/Toluene   | 100° C.   | 16 hrs        | 92:08             |
| 25         | S-CSA (1eq) | MeOH          | 80° C.    | 8 hrs         | 96:04             |
| 26         | S-CSA (1eq) | EtOH          | 80° C.    | 8 hrs         | 94:06             |
| 27         | S-CSA (1eq) | IPA           | 80° C.    | 8 hrs         | 95:05             |
| 28         | S-CSA (1eq) | THF           | Reflux    | 8 hrs         | 92:08             |

In experiments 1-7, three acids were tested. The reactions treated with tartaric acid consistently resulted in lower conversion than that treated with stronger acids such as CSA and p-TSA. In experiments 11-16 conducted in toluene or dioxane, CSA again offered a higher conversion ratio than that by L-tartaric acid. From experiments 8, 11-14, 19, and 20, it could be concluded that CSA, DDTA/DLTA in dioxane, toluene or DMSO at elevated temperature produced similar conversion results (S:R~1:1). CSA in DMSO heated to 140° C. was identified as an example of optimal conditions. Acetic acid was found to be ineffective.

All reactions carried out in the solvents with boiling point higher than 100° C. such as DMSO, toluene, and dioxane and at elevated reaction temperature, (experiments 11-14, 19, 20) generated relatively higher conversion ratios (S:R=~1:1). Exception was observed for the reaction carried out in DMF (experiments 17, 18; S:R=72:28). This result may be attributed to the slight Lewis basicity of DMF and its capability of neutralizing acid. All reactions conducted in THF which has a lower boiling point (67° C.) resulted in lower conversion ratios (experiments 1-7 and 28; S:R=~88:12). Dioxane is superior to ethyleneglycol dimethyl ether for the conversion. Interestingly, tartaric acid produced a better conversion ratio when carried out in dioxane, a more polar solvent with lower boiling point, than that in toluene, with opposite properties (experiments 15 and 16).

Among all experiments conducted, DMSO gives the cleanest result. Reactions carried out in both dioxane and toluene produced some impurity. However, when the reaction in toluene was purged with nitrogen, the reaction became cleaner. The improvement with nitrogen protection was not evident for the reactions carried out in DMSO and dioxane.

Generally elevated temperature was required in all reactions conditions. Experiments 11-14 were carried out with CSA under 100° C. and 120° C. for 8 hours. The conversion ratio was significantly higher (S:R=53:47) than that conducted at 67° C. (experiments 1 and 2). However, under identical condition tartaric acid did not produce similar results (experiments 15 and 16).

Although, toluene is a less polar and non-coordinating solvent than dioxane, similar conversion ratios were produced. On the other hand, THF and dioxane possess similar solvent polarity but very different conversion ratios (88:12 for THF and 53:47 for dioxane) were obtained. The results clearly indicate that a solvent with boiling point higher than 100° C. is essential for the reaction and the conversion is thermodynamic.

As shown in Table 3, dibenzoyl-D-tartaric acid (DDTA) is another effective acid to induce racemization. Reducing the quantity of the acid to 0.55 eq does not significantly change the S:R ratio (experiments 29 and 30).

TABLE 3

Summary of stoichiomery effect (reaction treated with DDTA)

| Experiment No | Equivalent | Solvent | Temp ° C. | ReactionTime | S:R   |
|---------------|------------|---------|-----------|--------------|-------|
| 29            | 1          | Dioxane | Reflux    | 4 hrs        | 52:48 |
| 30            | 0.55       | Dioxane | Reflux    | 3.5 hrs      | 54:46 |

All references cited herein are incorporated by reference. The present invention may be embodied in other specific forms without departing from the spirit or essential attributes of the invention.

We claim:

1. A method for racemizing an enantiomer of tofisopam to its racemate, the method comprising (a) reacting the enantiomer with one or greater base equivalent of an organic base at a temperature below 20° C. and (b) quenching the reaction with a proton source, thereby obtaining the racemate from the enantiomer.

2. The method according to claim 1, wherein the enantiomer is S-tofisopam.

3. The method according to claim 1, wherein the enantiomer is R-tofisopam.

4. The method according to claim 1, wherein the organic base is potassium t-butyloxide.

5. The method according to claim 1, wherein the proton source is water or camphorsultam.

6. A method for increasing the yield of a desired enantiomer of tofisopam over an undesired, the method comprising (a) obtaining the undesired enantiomer, (b) reacting the undesired enantiomer with one or greater base equivalent of an organic base at a temperature below 20° C., (c) quenching the reaction with a proton source thereby obtaining a racemate from the undesired enantiomer, and (d) isolating the desired enantiomer from the racemate of step (c).

7. The method according to claim 6, wherein the desired enantiomer is S-tofisopam.

8. The method according to claim 6, wherein the desired enantiomer is R-tofisopam.

9. The method according to claim 6, wherein the organic base is potassium-t-butyloxide.

10. The method according to claim 6, wherein the proton source is water.

11. A method for racemizing an enantiomer of tofisopam to its racemate, the method comprising (a) reacting the enantiomer with an organic or inorganic acid at an elevated temperature in a high temperature boiling organic solvent selected from the group consisting of dimethylsulfoxide, toluene and dioxane and (b) obtaining the racemate from the enantiomer.

12. The method according to claim 11, wherein the enantiomer is S-tofisopam.

13. The method according to claim 11, wherein the enantiomer is R-tofisopam.

14. The method according to claim 11, wherein the organic acid is selected from the group consisting of camphor sulfonic acid and dibenzoyl-D/L-tartaric acid.

15. A method for increasing the yield of a desired enantiomer of tofisopam from a racemic mixture, the method comprising (a) obtaining the undesired enantiomer, (b) reacting the undesired enantiomer with an organic acid at an elevated temperature in a high temperature boiling organic solvent selected from the group consisting of dimethylsulfoxide, toluene and dioxane, thereby obtaining a racemate from the undesired enantiomer, and (c) isolating the desired enantiomer from the racemate of step (b).

16. The method according to claim 15, wherein the desired enantiomer is S-tofisopam.

17. The method according to claim 15, wherein the desired enantiomer is R-tofisopam.

18. The method according to claim 15, wherein the organic acid is selected from the group consisting of camphor sulfonic acid and dibenzoyl-D/L-tartaric acid.

* * * * *